United States Patent [19]

Kendrick et al.

[11] Patent Number: 5,595,881
[45] Date of Patent: Jan. 21, 1997

[54] METHOD FOR THE DETECTION OF ANTIGEN PRESENTING CELLS

[75] Inventors: Teresa Kendrick, San Mateo; Bishwajit Nag; Prabha V. Mukku, both of Fremont; Somesh D. Sharma, Los Altos, all of Calif.

[73] Assignee: Anergen, Inc., Redwood City, Calif.

[21] Appl. No.: 288,143

[22] Filed: Aug. 9, 1994

[51] Int. Cl.$^6$ ............................. G01N 1/02; C12Q 1/68; C12Q 1/02
[52] U.S. Cl. ........................ 435/7.21; 435/6; 435/7.24; 435/29
[58] Field of Search ................................. 435/7.21, 7.24, 435/29, 6

[56] References Cited

FOREIGN PATENT DOCUMENTS

WO90/00063  6/1989  WIPO.

OTHER PUBLICATIONS

B. Nag et al, Jour. Immunological Methods, 169, 273–285, 1994.

Van Schooten, Wim C. A., et al. (1992) "Purified HLA Class II Peptide Complexes Can Induce Adherence and Activation of Peptide-Sepcific Human T Cell Clones", *The Journal of Immunology*, 148:1043–1048.

Binz, Hans, et al. (1979) "Binding of Purified, Soluble Major Histocompatibility Complex Polypeptide Chains Onto Isolated T–Cell Receptors", *J. Exp. Med.*, 150:1084–1097.

Coeshott, Claire M., et al. (1986) "Ia–Specific Mixed Leukocyte Reactive T–Cell Hybridomas: Analysis Of Their Specificity By Using Purified Class II MHC Molecules In A Synthetic Membrane System", *The Journal of Immunology*, 136(8):2832–2838.

Abromson–Leeman, Sara, et al. (1988) "Isolation of antigen–specific T cell clones from nonresponder mice", *Eur. J. Immunol.*, 18:145–152.

Laundy, G. J., et al. (1989) "Applications of Automated Simultaneous Double Fluorescence (SDF). II HLA Class I Phenotyping Using Immunomagnetically Separated T Lymphocytes", *Journal of Immunogenetics*, 16P:141–148.

Mantovani, V., et al. (989) "Nuova Tecnica Di Purificazione Linfocitaria Per La Tipizzazione HLA", *Boll. Soc. It. Biol Sper.*, LXV:967–973.

*Primary Examiner*—David Saunders
*Attorney, Agent, or Firm*—Townsend and Townsend and Crew LLP

[57] ABSTRACT

This invention provides a novel and rapid method for isolating MHC:antigen-restricted T cells. The method comprises the steps of (a) providing an isolated MHC:peptide complex wherein said complex is bound to a solid support; (b) contacting the complex with the biological sample containing T lymphocytes to form a MHC:peptide:T cell complex; (c) removing the MHC:peptide:T cell complex from the peripheral blood; and (d) separating the bound T lymphocytes from the MHC:peptide:T cell complex. The T-cells can be used to detect the presence, in a biological sample, of antigen presenting cells bearing a preselected MHC:antigen complex.

7 Claims, 1 Drawing Sheet

5,595,881

METHOD FOR THE DETECTION OF ANTIGEN PRESENTING CELLS

BACKGROUND OF THE INVENTION

This invention pertains to the field of immunology. More specifically, this invention provides a novel method of isolating pre-selected antigen-specific T-lymphocytes from a biological sample.

The isolation of T cells has been generally accomplished using lengthy procedures that involve a series of antigen stimulations in the presence of autologous antigen-presenting cells (APCs) which result in an increase in the clonal frequency of the T cells specific for the particular peptide bearing APC. The increased clonal frequency is a result of APC-induced proliferation of the T cell specific for the particular APC. Limiting dilution is often used to select for the growth of the targeted cell (see, for example, pp 3.15.9–12 in Current Protocols in Immunology, Coligan et al. (eds) (1991). The reliance on cell division to obtain a clonal population of cells makes this method a long and slow process requiring extensive labor and attention.

In addition, the binding of a specific antigenic peptide can occur with different affinities to any of the various and different MHC class II molecules expressed on APCs (Valli et al. J. Clin. Invest., 91:616–628 (1993). Thus there is no guarantee using prior art methods that T cells specific to a particular MHC restriction type will be isolated. The MHC restriction type of the T cells that are isolated must be determined empirically after isolation and specific MHC restriction types cannot be dictated prior to isolation.

SUMMARY OF THE INVENTION

This invention provides a novel and rapid method for isolating MHC:antigen-restricted T cells. This method does not rely on cell division or limiting dilution and the MHC restriction type may be dictated prior to the T cell isolation thus overcoming major limitations of prior art methods.

The method comprises the steps of (a) providing an isolated MHC:peptide complex wherein said complex is bound to a solid support; (b) contacting the complex with the biological sample containing T lymphocytes to form a MHC:peptide:T cell complex; (c) removing the MHC:peptide:T cell complex from the peripheral blood; and (d) separating the bound T lymphocytes from the MHC:peptide:T cell complex. In various preferred embodiments, the solid support is a magnetic bead, the biological sample is peripheral blood and the MHC:peptide complex is DR2:MBP84-102.

In another embodiment, this invention also provides a method of detecting the presence, in a biological sample, of antigen presenting cells bearing an antigen by (a) providing T cells specific for an MHC:antigen complex; (b) contacting the biological sample with the T cells; and (c) detecting changes in the proliferation rate of said T cells.

DETAILED DESCRIPTION

Figure 1:
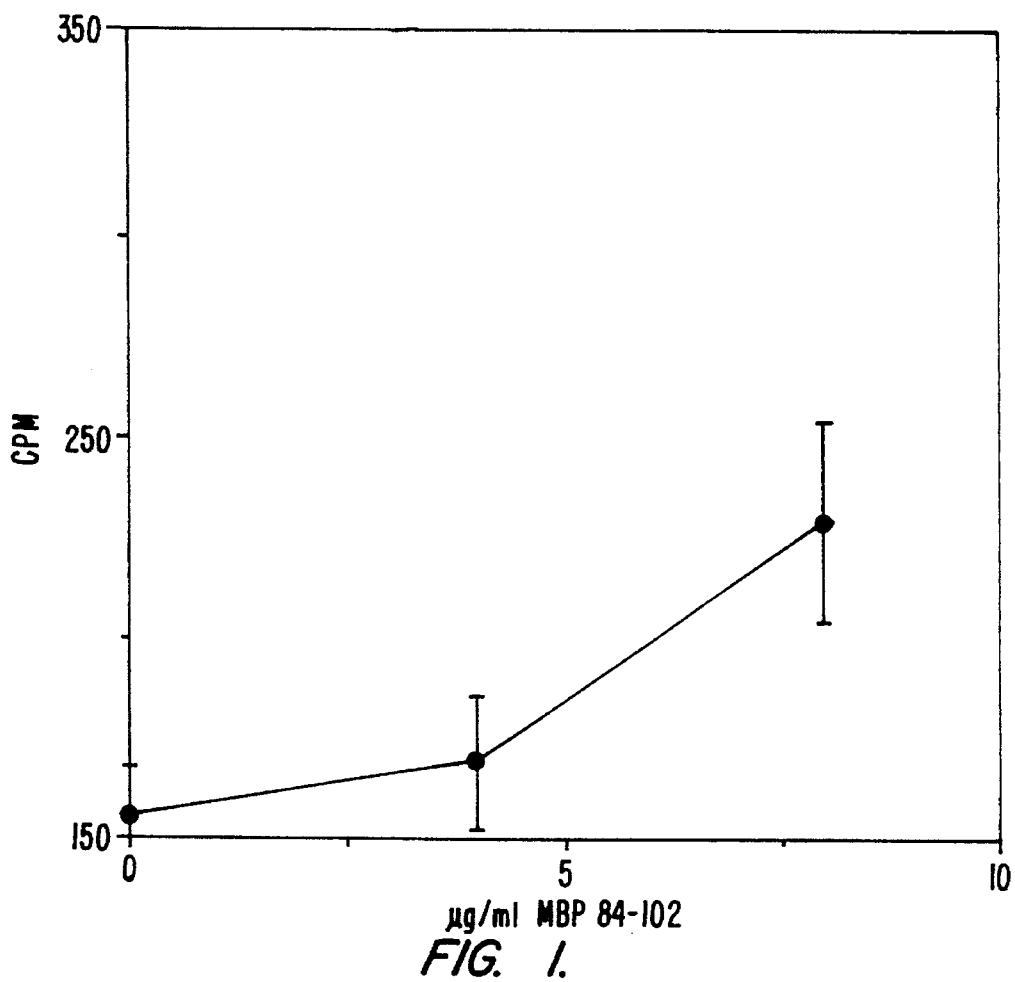
FIG. 1 shows the proliferation rate of isolated T cells, as measured by the uptake of [$^3$H]-thymidine, plotted as a function of the concentration of antigen and autologous APC in the culture. T cell proliferation rate shows a dose dependent response indicating the presence of antigen-specific T cells.

This invention provides a novel and rapid method for isolating specific major histocompatibility complex (MHC):antigen-restricted T cells. In contrast to the prior art, this method does not rely on cell division or limiting dilution and provides far more rapid isolation requiring significantly less labor and attention. In addition, unlike prior art isolation protocols, the MHC restriction type may be dictated prior to the T cell isolation.

It is desirable to isolate MHC:antigen-restricted T cells in a number of contexts. In adoptive immunotherapy, for example, lymphocytes are removed from a patient, expanded ex vivo, and then re-infused back into the patient where they augment the patient's native immune response (see U.S. Pat. No. 4,690,915 and Rosenberg et al. New Engl. J. Med., 313:1485–1492 (1985)). This approach has proven effective in the treatment of various cancers (see, for example, Rosenberg et al. New Engl. J. Med. 319:1676–1680 (1988)). Isolation and expansion of T cells specific for a particular MHC:antigen complex will increase the specificity and effectiveness of adoptive immunotherapeutic approaches.

Additionally, isolated MHC:antigen-restricted T cells may also be used as a diagnostic to screen for the occurrence of a particular MHC:antigen complex and thus detect the presence or absence of an early immune response. Early detection of the presence or absence of an immune response will facilitate selection of a particular treatment regiment in a variety of pathological conditions such as autoimmune diseases, allergies, allograft rejection, infections diseases, and the like. In a diagnostic of this type, the isolated T cells are used both as a means of detection and as reporters. The T cells proliferate when contacted with the MHC:antigen complex for which they are specific. This proliferation is easily detected as an increase in cell number or as an increase in growth rate measured, for example, by the rate of uptake of a metabolic substrate (e.g. [$^3$H]-thymidine). Thus, the presence or absence of MHC bound antigen can be detected by exposing the isolated T cells to a tissue sample (e.g., peripheral blood) and monitoring their proliferation rate.

Finally, isolation of MHC:antigen-restricted T cells provides a homogeneous source of T cell receptors. A homogeneous source aids the elucidation of structure-function relationships of particular receptors. It also facilitates the development of solubilized T cell receptors which are of use in a number of therapeutic applications. (See, for example, PCT Patent Application No. 9201715 for Davis, et al. and U.S. Pat. No. 5,283,058).

As used herein, the phrase "isolated T cell(s)" refers T cells that are substantially or essentially free from components which normally accompany them as found in their native state. In particular the isolated T cells are essentially free from other T cells having a different antigen specificity or MHC restriction. Thus "isolation of T cells having a pre-selected antigen specificity and MHC restriction" refers to the preferential selection and removal of T cells having an a priori determined particular antigen specificity and MHC restriction from a population of T cells that is heterogeneous in their antigen specificity and MHC restriction.

The T cell isolation method of this invention relies on the creation of a complex comprising an effective portion of one or more MHC encoded antigen-presenting glycoproteins bound to a peptide representing a fragment of an autoantigen or other antigenic sequence (i.e., an antigenic peptide). This complex is referred to herein as an MHC:peptide complex. Methods of forming MHC:peptide complexes are described by Sharma et al. *Proc. Natl. Acad. Sci. USA*, 88:11465–11469 (1991) and in U.S. Pat. Nos. 5,216,132 and 5,194,425. The MHC:peptide complex is immobilized on a solid support and then exposed to a biological sample from which the T cells are to be isolated. Those T cells containing receptors specific for the particular MHC:peptide complex bind to the complex forming a MHC:peptide:T cell complex. The solid supports bearing the MHC:peptide:T cell complex are then isolated from the biological sample. The bound MHC:antigen-restricted T cells are separate from the MHC:peptide:T cell complex when the complexes are cultured at 37° C. The T cells isolated in this manner may be expanded in culture to provide a population of T cells specific for the MHC:peptide complex.

As used herein, the phrase "T cells specific for a pre-selected MHC:peptide complex" or T cells that "bind specifically to a MHC:peptide complex" refers to a binding reaction which is determinative of the presence of a particular antigen specific, MHC-restricted T cell in the presence of a heterogeneous population of T cells and other biologics. Thus, under designated immunoassay conditions, the specified T cells bind to a particular pre-selected MHC:peptide complex and do not bind in a significant amount to other MHC:peptide complexes present in the sample. Specific binding T cells or T cells specific for a preselected MHC:peptide complex refers to those T cells in a heterogenous population of T cells which bind to a particular pre-determined MHC:peptide complex with greater specificity and affinity than at least 80%, more preferably at least 90%, and still more preferably at least 95% of the T cells in the population.

A T cell is "reactive with" or "binds to" an MHC:peptide complex if it interacts with the MHC:peptide complex. Typically, the binding interactions between T cell and MHC:peptide complex involve reversible noncovalent associations such as electrostatic attraction, Van der Waals forces and hydrogen bonds. This interaction is analogous to a chemical reaction in which two reactants come together to form a product. In the case of the T cell-MHC:peptide complex interaction, the product of the interaction is an MHC:peptide-T cell. In a population of MHC:peptide-specific T cells selected using the method of this invention, at least 80% of the cells, more preferably at least 90% and even more preferably at least 95% of the T cells are specific for the MHC:peptide complex.

Formation of MHC/Peptide Complex.

1) The MHC Component

As explained above, this invention requires the formation of an MHC:peptide complex. The MHC component of the MHC:peptide complex is an effective portion of an MHC-encoded antigen-presenting glycoprotein. This component is readily isolated from cells which produce such MHC glycoproteins using the methods and procedures set forth herein and in copending patent application U.S. Ser. No. 08/227, 372 and in Nag et al. *J. Immunol. Meth.*, 169:273–285 (1994), which are incorporated herein by reference.

The glycoproteins encoded by the major histocompatibility complex in both human and murine systems are generally classified as either Class I or Class II glycoproteins. Class I glycoproteins are found on the surfaces of all cells and are primarily recognized by cytotoxic T cells, while Class II glycoproteins are found on the surface of several cells, including accessory cells such as macrophages, and are involved in the presentation of antigens to T helper cells. A number of the MHC proteins have been isolated and characterized. For a general review of MHC glycoprotein structure and function, see, e.g., *Fundamental Immunology* (2d Ed., W. E. Paul, (ed.), Ravens Press, N.Y. (1993)), which is incorporated herein by reference.

The term "MHC component" as used herein refers to one or more MHC glycoproteins or an effective portion of one or more MHC glycoproteins (i.e., comprising an antigen binding site or sites and the sequences necessary for recognition by the appropriate T cell receptor) which is in other than its native state (i.e., not associated with the cell membrane of the cell that normally expresses MHC). As described in detail below, the MHC component is preferably solubilized from an appropriate cell source. For human MHC molecules, human lymphoblastoid cells are particularly preferred as sources for the MHC component.

The MHC glycoprotein portions of the complexes of the invention can be obtained by isolation from lymphocytes and screened for their ability to bind the desired peptide antigen. The lymphocytes are preferably obtained from the species from which it is desired to isolate MHC:antigen-specific T cells. For example, where human T cells will be isolated, the MHC-encoded glycoprotein component will preferably be obtained from human B cells which have been immortalized by transformation with a replication deficient Epstein-Barr virus, utilizing techniques known to those in the art.

MHC glycoproteins have been isolated from a multiplicity of cells using a variety of techniques including, for example, solubilization by treatment with papain, by treatment with 3M KCl and by treatment with detergent. In a preferred method, detergent extraction of Class II protein from lymphocytes followed by affinity purification is used. The detergent can subsequently be removed by dialysis or through the use of selective binding beads, e.g., Bio Beads.

Methods for purifying the murine I-A (Class II) histocompatibility proteins have been disclosed by Turkewitz, et al., *Molecular Immunology*, 20:1139–1147 (1983), which is incorporated herein by reference. These methods, which are also suitable for Class I molecules, involve the preparation of a soluble membrane extract from cells containing the desired MHC molecule using nonionic detergents, such as, for example, NP-40, TWEEN™ 80 and the like. The MHC molecules are then purified by affinity chromatography, using a column containing antibodies raised against the desired MHC molecule. Use of 0.02% TWEEN™ 80 in the elution buffer is helpful for eliminating aggregation of the purified molecules.

The isolated antigens encoded by the I-A and I-E subregions have been shown to consist of two noncovalently bonded peptide chains: an alpha chain of 32–38 kD and a beta chain of 26–29 kD. A third, invariant, 31 kD peptide is noncovalently associated with these two peptides, but it is not polymorphic and does not appear to be a component of the antigens on the cell surface (Sekaly, *J. Exp. Med.* 164:1490–1504 (1986), which is incorporated herein by reference). The alpha and beta chains of seven allelic variants of the I-A region have been cloned and sequenced.

The human Class I histocompatibility proteins have also been studied. The MHC of humans (HLA) on chromosome 6 has three loci, HLA-A, HLA-B, and HLA-C, the first two of which have a large number of alleles encoding alloantigens. These are found to consist of a 44 kD subunit and a 12 kD beta$_2$-microglobulin subunit which is common to all antigenic specificities. Isolation of these detergent-soluble HLA antigens was described by Springer, et al., *Proc. Natl. Acad. Sci.* USA 73:2481–2485 (1976); Clementson, et al., in "Membrane Proteins" (Azzi, A., ed.); Bjorkman, P., Ph.D. Thesis Harvard (1984), all of which are incorporated herein by reference.

Alternatively, since the amino acid sequences of a number of MHC glycoproteins are known and the genes have been cloned, one may express the desired MHC glycoprotein in a recombinantly engineered cell such as, for example, bacteria, yeast, insect (especially employing baculoviral vectors), and mammalian cells using conventional techniques know to those of skill in the art. It is expected that those of skill in the art are knowledgeable in the numerous expression systems available for expression of the DNA encoding the MHC glycoproteins.

In brief, the expression of natural or synthetic nucleic acids encoding MHC polypeptides will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the perilipin proteins. To obtain high level expression of a cloned gene, it is desirable to construct expression plasmids which contain, at the minimum, a strong promoter to direct transcription, a ribosome binding site for translational initiation, and a transcription/translation terminator.

Prokaryotic expression systems suitable for expressing the MHC glycoproteins include, but are not limited to, the following: *E. coli, Bacillus sp.* and Salmonella (Palva, et al., *Gene* 22:229–235 (1983); Mosbach, et al., *Nature* 302:543–545 (1983), with *E. coli* expression systems being presently preferred. Moreover, eukaryotic expression systems suitable for expressing the MHC glycoproteins include, for example, mammalian, yeast or insect cells.

The transformed cells are then cultured under conditions favoring expression of the MHC sequence and the recombinantly produced protein recovered from the culture. The recombinant MHC protein can be purified using conventional techniques known to those of skill in the art. In particular, it will be understood by those of skill that a metal binding domain, e.g., a sequence encoding a polyhistidine sequence, can be incorporated into the nucleic acid encoding the MHC polypeptides prior to their expression using standard techniques. Subsequently, the recombinantly produced MHC polypeptides containing the metal binding domain can be purified using metal chelate chromatography. (See, section pertaining to "Metal Chelate Affinity Chromatography," infra.)

For a general overview of the techniques employed in the recombinant expression of MHC glycoproteins, see, for example, Sambrook, et al., *Molecular Cloning: A Laboratory Manual* (2nd Ed., Vols. 1–3, Cold Spring Harbor Laboratory (1989)), *Methods in Enzymology*, Vol. 152. *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987), all of which are incorporated herein by reference.

2. The Peptide Component

Formation of the MHC:peptide complex of course requires provision of a peptide component derived from the antigen against which the isolated antigen-specific T cell will be directed. One of skill in the art will recognize that the claimed method of T cell isolation will function with any peptide capable of being bound by an MHC glycoprotein and having an epitope recognizable by a T cell.

Antigenic proteins as well as autoantigenic proteins and tissues from a number of autoimmune diseases are well known. For example, T cell epitopes have been identified in honey bee venom allergens, dust mite allergens, and ragweed allergens. Similarly, T cell epitopes have been identified in a number of infectious diseases including, for example, tetanus toxoid and pertussis toxin.

A large number of antigenic proteins or tissues for autoimmune diseases are also well known. In experimentally induced autoimmune diseases, for example, the following antigens involved in pathogenesis have been characterized: native type-II collagen has been identified in collagen-induced arthritis in rat and mouse, and mycobacterial heat shock protein in adjuvant arthritis (Stuart, et al., (1984), *Ann. Rev. Immunol.* 2:199–218; van Eden, et al., (1988), *Nature* 331:171–173.); thyroglobulin has been identified in experimental allergic thyroiditis (EAT) in mouse (Maron, et al., (1988), *J. Exp. Med.* 152:1115–1120); acetyl choline receptor (AChR) has been identified in experimental allergic myasthenia gravis (EAMG) (Lindstrom, et al. (1988), *Adv. Immunol.* 42:233–284); and myelin basic protein (MBP) and proteolipid protein (PLP) have been identified in experimental allergic encephalomyelitis (EAE) in mouse and rat (See Acha-Orbea, et al., supra). In addition, target antigens have been identified in humans: type-II collagen has been identified in human rheumatoid arthritis (Holoshitz, et al., (1986), *Lancet ii:*305–309); and acetyl choline receptor in myasthenia gravis (Lindstrom, et al., (1988), supra). All of the above references are incorporated herein by reference.

It is believed that the presentation of antigen by the MHC glycoprotein on the surface of antigen-presenting cells (APCs) occurs subsequent to the hydrolysis of the antigenic proteins into smaller peptide units. The location of these smaller segments within the antigenic protein can be determined empirically. These segments are thought to be about 8 to about 18 residues in length and to contain both the agretope (recognized by the MHC molecule) and the epitope (recognized by the T cell receptor on the T-helper cell). The epitope itself is a contiguous or non-contiguous sequence of about 5 to about 6 amino acids which recognizes the antigen-specific receptor of T-helper cells. The agretope is a continuous or non-contiguous sequence which is responsible for the association of the peptide with the MHC glycoproteins.

The peptide component of the MHC:peptide complex must contain both an agretope that permits binding by an MHC glycoprotein and an epitope that permits recognition by a T cell. The peptide fragment of an antigen suitable for formation of the MHC:peptide complex may be empirically determined. First, a set of labeled test peptides is prepared and those which bind to an MHC in planar lipid membranes containing MHC proteins are shown to contain the agretope. The identified agretope-bearing peptides are then prepared by conventional solid phase synthesis, and the subset which also contains epitopes for the disease-inducing T-helper cell clones is determined by incubation of the candidate peptides with murine antigen-presenting cells (APC) (or with isolated MHC complex) and spleen or lymph node T cells from mice immunized with the full length protein. Successful candidates will stimulate T cell proliferation in this system. This second, smaller subset represents the suitable peptide component.

This empirical process of determining the relevant 8–18 amino acid subunits is illustrated in more detail below using the alpha subunit of the acetylcholine receptor (AChR) of skeletal muscle which is known to be involved in myasthenia gravis. It is will be apparent to those skilled in the art that, using the process set forth below, one can readily determine the relevant peptide component for use in the claimed T cell isolation method.

In myasthenia gravis (MG), autoantibodies against the alpha subunit of the acetylcholine receptor (AChR) are associated with the autoimmune response directed at the AChR. Eighty five percent of MG patients have autoantibodies reactive with the alpha subunit. Of these, 60% have antibodies that bind to a peptide segment of the alpha subunit called the main immunogenic region (MIR) which is located between residues 60 and 80 (Tzartos and Lindstrom, *Proc. Natl. Acad. Sci.* USA (1980) 77:755). The peptide segments recognized by autoreactive human T cells are also located on the alpha subunit (Hohfield, et al., *Proc. Natl. Acad. Sci.* USA (1987). The epitopes recognized by these T cells lie between residues 1–30, 125–147, 169–181, 257–271 and 351–368. In addition, in humans the AChR peptides 195–212 and 257–269 have been partially characterized as epitopes in myasthenia gravis patients of the HLA-DR5 and HLA-DR3, DQw2 MHC haplotypes, respectively (See, Acha-Orbea (1989), supra).

The peptides carrying agretopes permitting presentation of the epitopes associated with the alpha subunit of this receptor are readily determined. For example, determination of the appropriate peptides in a mouse model is carried out as follows.

Strains of mice, which when immunized with *Torpedo californicus* AChR develop a disease with many of the features of human myasthenia gravis, are used as the model. MHC Class II glycoproteins are isolated from spleen cells of these mice using lectin and monoclonal antibody affinity supports. The purified MHC Class II proteins are incorporated into phospholipid vesicles by detergent dialysis. The resultant vesicles are then allowed to fuse to clean glass cover slips to produce on each cover slip a planar lipid bilayer containing MHC molecules (See, Brian and McConnell, *Proc. Natl. Acad. Sci.* USA (1984) 81:6159, which is incorporated herein by reference).

One cover slip containing MHC Class II molecules embedded in the adherent planar lipid membrane is placed in each well of several 24-well culture plates. Each one of the approximately 40 overlapping 20-residue synthetic peptides corresponding to the alpha subunit sequence and containing one or more radiolabeled amino acid residues (prepared as described below) is placed in a well with cover slip and phosphate buffered saline (PBS), and allowed to incubate several days. The extent of binding of peptide in the MHC Class II glycoprotein antigen binding site is measured by the amount of radioactivity incorporated into the MHC Class II-planar lipid membrane on the cover slip versus planar lipid membrane alone. Specific incorporation of radioactivity indicates that the bound peptide contains an agretope (MHC Class II peptide binding site) of one of the several species of MHC Class II molecules present in the planar lipid membrane. In this manner, the set of agretopes for the alpha subunit of AChR is defined for the mouse strain that displays the symptoms of MG upon immunization with AChR or purified alpha subunit.

Next, each of the alpha subunit synthetic peptide segments that contain an agretope is again incorporated into the antigen binding site of isolated MHC Class II proteins embedded in planar lipid membranes on cover slips. One cover slip is added to each well of a 24-well culture plate, and spleen cells from mice immunized against AChR (and from which strain the adherent MHC Class II proteins were isolated) are added to each well. T cell hybridoma proliferation, as measured by tritiated thymidine uptake into DNA, indicates that the MHC Class II protein-bound peptide contains both an agretope and an epitope for binding to the T cell. Activation of T cell clones is determined by measuring IL-3 production (See, Quill, et al., supra).

The Dupont apparatus and technique for rapid multiple peptide synthesis (RAMPS) are used to synthesize the members of a set of overlapping (10 residue overlap), 20-residue peptides from the alpha subunit of *Torpedo californicus* AChR. The sequence of this peptide is known. One or more radioactive amino acids is incorporated into each synthetic peptide. The pentafluorophenyl active esters of side chain-protected, FMOC amino acids are used to synthesize the peptides, applying standard stepwise solid phase peptide synthetic methods, followed by standard side chain deprotection and simultaneous release of the peptide amide from the solid support.

Alternatively, the overlapping sequences which include the putative segments of 8–18 amino acids of the antigenic protein, such as acetylcholine receptor protein, can be synthesized using the method of Geysen, et al., *J. Immun. Meth.* (1987) 102:274, which is incorporated herein by reference. The synthesized radiolabeled peptides are subsequently tested by incubating them individually (on the plates) with purified MHC proteins which have been formulated into lipid membrane bilayers as described above.

Using the above disclosed procedure, one of skill in the art can readily determine the relevant 8–18 amino acid subunit for the antigens associated with other disease states, particularly in autoimmune diseases. For example, in multiple sclerosis (MS), which results in the destruction of the myelin sheath in the central nervous system, it is known that myelin basic protein (MBP) (i.e., the major protein component of myelin) is the principal autoantigen. Pertinent segments of the MBP protein can also be determined empirically using the procedure described above and a strain of mice which develops experimental allergic encephalitis (EAG) when immunized with bovine myelin basic protein.

Similarly, systemic lupus erythematosus (SLE), although having a complex systemology, is known to result from an autoimmune response to red blood cells. Peptides which are the antigenic effectors of this disease are found in the proteins on the surface of red blood cells. Rheumatoid arthritis (RA), a chronic inflammatory disease, results from an immune response to proteins found in the synovial fluid. Insulin-dependent diabetes mellitus (IDDM) results from autoimmune attack on the beta cells within the Islets of Langerhans which are responsible for the secretion of insulin. Circulating antibodies to Islets cells surface antigens and to insulin are known to precede IDDM. Critical peptides in eliciting the immune response in IDDM are believed to be portions of the insulin sequence and the beta cell membrane surface proteins.

In a preferred embodiment, in order to facilitate separation of the MHC-peptide complexes of interest from both uncomplexed MHC molecules and other endogenous MHC-peptide complexes, at least one metal-chelating amino acid is incorporated into the autoantigenic or antigenic peptide of interest. As used herein, the term "metal-chelating amino acid" is used to refer to an amino acid that is capable of participating in metal binding, i.e., an amino acid that is capable of forming a chelate or complex with a metal ion. Metal-chelating amino acids include, but are not limited to, the following: glycine, tyrosine, cysteine, histidine, arginine, lysine, asparagine and methionine. In a presently preferred embodiment, histidine is the metal-chelating amino acid incorporated into the antigenic peptide. Moreover, as will be explained below, in one embodiment, from two to about ten metal-chelating amino acids (e.g., histidines) are incorporated into the antigenic peptide.

Since the relevant antigenic sequences are relatively short in length (typically less than 25 amino acids), they can be readily synthesized using standard automated methods for peptide synthesis. In doing so, at least one metal-chelating amino acid is incorporated at either the N- or the C-terminus of the protein. Preferably, from two to about ten metal-chelating amino acids are incorporated into the antigenic peptide. More preferably, about six metal-chelating amino acids are incorporated into the antigenic peptide. Alternatively, the antigenic peptide tagged with at least one metal-chelating amino acid can be made recombinantly using isolated or synthetic DNA sequences.

3. Formation of the MHC-Peptide Complex.

Once the MHC component has been isolated and the antigenic peptide has been synthesized, these two elements can be associated with one another to form an MHC:peptide complex using standard means known in the art. The antigenic peptides can be associated noncovalently with the pocket portion of the MHC protein by, for example, mixing the two components together. This is typically done in an aqueous buffer that preserves the native conformation of the respective molecules. Methods of producing MHC:peptide complexes are described by Sharma et al. *Proc. Natl. Acad. Sci. USA*, 88:11465–11469 (1991) and in U.S. Pat. Nos. 5,216,132 and 5,194,425. After association of the two components, excess peptide can be removed using a number of standard procedures, such as, for example, by ultrafiltration or by dialysis.

4. Purification of the MHC-Peptide Complex.

Once the MHC and peptide components are associated, it is necessary to separate the MHC:peptide complex of interest from both uncomplexed MHC molecules and other endogenous MHC-peptide bound complexes. The MHC:peptide complexes may be purified by a number of means known to those of skill in the art. In one method, the MHC:peptide complex may be isolated using a biotin-avidin system where the antigenic peptide contains a long chain thiol cleavable biotin moiety. (See, Demotz, et al., *Proc. Nat'l Acad. Sci.* U.S.A. 88:8730–8734, which is incorporated herein by reference.)

The preferred purification method, however, is based on the use of metal chelate affinity chromatography as described in copending patent application U.S. Ser. No. 08/227,372 and in Nag et al. *J. Immunol. Meth.*, 169:273–285 (1994), which are incorporated herein by reference. See, also, Lonnerdal and Keen, *J. Appl. Biochem*, 4:203–208 (1982); Sulkowski, *Trends in Biotechnology* 3:1–7 (1985).

Generally, metal chelate affinity chromatography takes advantage of the reversible interaction between metal ions (such as, for example, $Cu^{2+}$, $Zn^{2+}$, $Ni^{2+}$, etc.) and electron donor groups situated on the surface of proteins, especially the imidazole side-chain of histidine. By immobilizing metal ions on a chromatography solid support or matrix through the use of a chelating ligand (i.e., by forming a chelate resin), a protein having an accessible electron donor group can be separated from protons lacking such groups. The protein binds to the immobilized metal ions when the pH is such that the electron donor group is at least partially unprotonized. The bound protein can subsequently be eluted using a number of different techniques such as, for example, by competitive elution, by lowering the pH or, by using strong chelating agents.

Metal ions suitable for use in accordance with the present purification method include, but are not limited to, the first-row transitions metals. The first-row transition metals include, for example, $Cu^{2+}$, $Zn^{2+}$, $Ni^{2+}$, $Co^{2+}$ and $Fe^{3+}$. In a presently preferred embodiment, $Ni^{2+}$, $Cu^{2+}$ and $Zn^{2+}$ are the metal ions used. It has been found that these metals readily form a complex or chelate with metal-chelating amino acids and thus, they can be used to separate those proteins having a metal-chelating amino acid(s) from those which do not.

Metal-chelating amino acids suitable for use in accordance with the present method include those that are capable of participating in metal binding, i.e., those amino acids that are capable of forming a chelate or complex with a metal ion. Metal-chelating amino acids include, but are not limited to, the following: glycine, tyrosine, cysteine, histidine, arginine, lysine, asparagine and methionine. In a presently preferred embodiment, histidine is the metal-chelating amino acid incorporated into the antigenic peptide. Since histidine is a relatively rare amino acid, accounting for only about 2% of the amino acids in most globular proteins (Klapper, M. H., *Biochem. Biophys. Res. Commun.* 78:1018 (1977)), selective separation of histidine-tagged polypeptides from a complex mixture can be achieved under both native and denatured conditions. Moreover, in a presently preferred embodiment, from two to about ten metal-chelating amino acids are incorporated into the antigenic peptide using standard automated methods for peptide synthesis. In a more preferred embodiment, about six metal-chelating amino acids are incorporated into the antigenic peptide.

A chelating ligand is used to link the metal ion to the solid support or chelating matrix. The particular chelating ligand employed is not a critical aspect of the present invention. Any chelating ligand can be used provided that the ligand strongly complexes the metal ions while permitting reversible interactions between the metal ions and the protein to be purified. Chelating ligands suitable for use in accordance with the present method include, but are not limited to, the following: iminodiacetic acid ("IDA"), N,N,N'-tris(carboxymethyl)ethylenediamine ("TED"), N-carboxymethyl aspartate, N,N,N,N,N-carboxymethyl tetraethylenepentamine and nitrilotriacetic acid ("NTA"). Certain of these chelating ligands are presently preferred, namely, IDA, TED and NTA. When $Ni^{2+}$ is the metal ion used, NTA, i.e., nitrilotriacetic acid, is the presently preferred chelating ligand. When charged with $Ni^{2+}$, nitrilotriacetic acid is especially useful for the purification of proteins containing neighboring histidine residues. The use of nitrilotriacetic acid as a chelating ligand is described in U.S. Pat. No. 5,047,513, which is incorporated herein by reference.

The chelating ligand is covalently bound to a solid support or, alternatively, a chelating matrix using conventional methods and techniques known to and understood by those skilled in the art. The solid support, having the chelating ligand bound thereto, is subsequently charged with a metal ion. As with the chelating ligand, the solid support employed is not a critical aspect of the present invention. Materials suitable for use as the solid support include those materials commonly used in affinity and gel chromatography. Examples of such materials include, but are not limited to, the following: dextran, agarose, cellulose, polystyrene, polyacrylamide, and their derivatives. In a presently preferred embodiment, agarose or a derivative thereof (such as, for example, Sepharose™ (Pharmacia Biosystems, Uppsala, Sweden)) is used as the solid support.

The solid support, charged with the metal ion, can be used batch-wise or in a chromatography column. In a presently preferred embodiment, the solid support is packed into a column (e.g., 14.5 cm×1.6 cm), and equilibrated with an aqueous buffer that does not form chelates with the metal ion employed. It will be readily apparent to those skilled in the art that the dimensions of the column can be varied depending upon the quantity of protein to be purified. Moreover, it will be readily apparent to those of skill in the art that a number of different aqueous buffers can be used provided they do not form chelates with the metal ion employed. Equilibration buffers suitable for use in the present method include, for example, a sodium or potassium phosphate buffer (pH 7–8) or a Tris-HCl buffer (pH 7.0).

Once formed, the MHC-peptide complexes (in equilibrating buffer) are contacted with the solid support in either a batch or column format. The MHC-peptide complexes containing a metal-chelating amino acid in the peptide component of the complexes will chelate with the metal ion and thus, be bound to the solid support. The solid support is then washed with equilibrating buffer to remove the uncomplexed MHC molecules and other MHC-peptide complexes, neither of which will bind to the solid support due to the absence of a metal-chelating amino acid. Additionally, the solid support can be washed with a number of different reagents to remove residual contaminations due to disulfide cross links, hydrophobic interactions, low affinity binding to the resin, etc. As such, the equilibrating buffer can contain a denaturing agent or a detergent, such as, for example, guanidine, NaCl, ethanol, glycerol, urea, Tween or Triton™.

Finally, the bound MHC-peptide complexes of interest are eluted from the column by washing the solid support with an elution buffer. The elution buffer can be of a constant pH or can be applied as a pH gradient. The elution buffer can contain either a Lewis acid, i.e., an electron acceptor, which competes with the metal for the protein, or a Lewis base, i.e., an electron donor, which competes with the protein for the metal. In a presently preferred embodiment, the elution buffer used is 0.05M imidazole; imidazole will compete with the protein for the metal coordination sites thereby displacing the MHC-peptide. The optimal elution conditions are dependent on the amount and type of impurities present, the amount of material to be purified, the column dimensions, etc. Such conditions are readily determined on a case by case basis by those of ordinary skill in the art.

Binding of the MHC/Peptide to a Solid Support

In a preferred embodiment of this invention, the isolated MHC:peptide complex is immobilized by attaching it to a solid support. Various solid supports are well known to those of skill in the art. A suitable support is one which provides a functional group for the attachment of the MHC:peptide complex either directly or indirectly through a linker. Typically a solid support comprises a solid phase material derivatized with functional groups to facilitate the chemical coupling of the MHC:peptide complex or a linker joined to the MHC:peptide complex. In general, the solid support should be inert to the reagents to which it will be exposed. Suitable solid support materials include, but are not limited to, polacryloylmorpholide, silica, controlled pore glass (CPG), polystyrene, polystyrene/latex, carboxyl modified teflon, derivatized magnetic beads, and even glass or polymer cell culture dishes and the like.

The MHC:peptide complexes may be immobilized on the solid support either directly through a covalent bond (i.e., through the terminal carboxyl or amino groups of the MHC-encoded glycoprotein) or indirectly through one or more linkers. The term linker, as used herein refers to a single molecule or a complex of molecules that join the MHC:peptide complex to the solid support. The linker may be joined to the MHC:peptide complex, the solid support, or to other linker molecules through covalent bonds, ionic bonds, van der Waals interactions, or hydrophobic interactions either individually or in combination. Linkers suitable for joining peptides are well known to those of skill in the art. Generally linkers are either hetero- or homo-bifunctional molecules that contain two reactive sites that may form a covalent bond with the MHC:peptide complex and with the solid support respectively. A number of linker molecules are well known to those of skill in the art. For example, MHC:peptide complex may be joined to the solid support by a peptide linker, by a straight or branched chain carbon chain linker, or by a heterocyclic carbon linker. Heterobifunctional cross linking reagents are well known to those of skill in the art. See, for example, Lerner et al. *Proc. Nat'l. Acad. Sci. USA*, 78:3403–3407 (1981) and Kitagawa et al. *J. Biochem.*, 79:233–236 (1976) which are incorporated herein by reference.

In a preferred embodiment the linker comprises a first monoclonal antibody chemically conjugated to the solid support, where the first monoclonal antibody is specific to a component of a second monoclonal antibody which is, in turn, specific for a component of the MHC:peptide complex. Thus, for example, magnetic beads may be chemically conjugated with a rat anti-mouse IgG (e.g. $IgG_{2a}$) which, in turn, binds to mouse anti-human MHC antibody which binds to a human MHC:peptide complex.

Isolation of MHC:Antigen Specific T cells.

To isolate MHC:antigen-specific T cells, a biological sample containing T cells is incubated with the solid support-bound MHC:peptide complex. A "biological sample" refers to any sample obtained from a living organism or from an organism that has died. Examples of biological samples include body fluids and tissue specimens. In the case of microorganisms a biological sample may include samples containing many entire organisms.

T cells present in the biological sample that are specific for the MHC component and the bound peptide will bind to the MHC:peptide complex forming a MHC:peptide:T cell complex. The MHC:peptide:T cell complex is then removed from biological sample. This may be accomplished by simply washing away the biological sample while retaining the solid support. Alternatively, the solid support bearing the MHC:peptide:T cell complex may be removed from the biological sample. In a preferred embodiment, where the solid support is a magnetic bead, the separation may be accomplished magnetically.

The MHC:peptide-specific T cells are separate from the spontaneously from the complex when it is incubated overnight at 37° C. The isolated T cells may then be grown in standard culture media (e.g. RPMI 1640, 10% fetal bovine serum, 2 mM L-glutamine, 20 U/ml recombinant human interleukin-2). Interleukin-2 is added in order to reverse potential anergy due to lack of T cell costimulation via B7(APC)-CD28(T cell) interactions.

Verifying the MHC:Peptide Specificity of the Isolated T cells

To verify the specificity of the isolated T cells, the T cells may be challenged, in culture, with the particular peptide fragment that was bound to the MHC-encoded glycoprotein and autologous antigen presenting cells (APCs). If the T cells are specific for the particular peptide MHC class present on the APCs, they will proliferate in response to the challenge.

T cell proliferation may be measured by a number of means well known to those of skill in the art. Typical methods involve either measuring the increase in cell number or alternatively, measuring changes in metabolic rate as determined by the rate of uptake of a labeled metabolic substrate. While a number of labeled metabolic substrates are well known to those of skill, [$^3$H]-thymidine is preferred. Thus, if the T cells are specific to the particular peptide and MHC class, they will show a MHC/peptide dose-dependent increase in the rate of [$^3$H]-thymidine uptake.

The following examples are offered by way of illustration, not by way of limitation.

EXAMPLE 1

Isolation of T Cells Specific To MBP(84-102)

Complexes of major histocompatibility complex class II encoded glycoprotein HLA DR2 (HLA DRB1*1501 and DRB5*0101) and myelin basic protein peptide analog, $His^{77-82}Y^{83}$MBP84-102 were isolated as described in copending patent application U.S. Ser. No. 08/227,372 and by Nag et al. *J. Immunol. Meth.* 169:273–285 (1994) which are incorporated herein by reference. HLA DR2 refers to the DR2 glycoproteins of the human MHC complex. The myelin basic protein analog $His^{77-82}Y^{83}$MBP84-102 is a peptide containing six histidines at the amino terminus followed by a tyrosine and then residues 84 through 102 of the myelin basic protein. The specifically loaded complexes, designated DR2:MBP84-102 were purified from uncomplexed molecules or complexes with nonspecifically bound peptides by metal chelate affinity chromatography as described by Nag et al. Id.

The DR2:MBP84-102 complex was then immobilized onto magnetic beads. This was accomplished by incubating magnetic beads conjugated to rat anti-mouse $IgG_{2a}$ (Dynal, Inc. Great Neck, N.Y., USA)) with mouse anti-human MHC class II DR monoclonal antibody, L243 (ATCC Deposit Number HB55) and DR2:MBP84-102 at 37° C. for 1 hour in a phosphate buffer solution (0.1M NaPO4, pH 7.5, 0.1% human serum albumin, 0.02% $NAN_3$). The beads, now bearing the DR2:MBP84-102 complex were then washed four times in RPMI 1640 medium (Gibco-BRL, Grand Island N.Y., USA).

Whole blood was obtained from a donor previously typed as DR2 positive. Mononuclear cells were separated over a ficoll gradient. The cells were cultured for three days in a culture medium consisting of RPMI supplemented with 10% fetal bovine serum, 2 µM L-glutamine, and 10 µg/ml phytohemaglutinin (Gibco-BRL, Grand Island N.Y., USA), then washed with the RPMI 1640 and then maintained in the culture medium described above supplemented with 20 U/ml of recombinant human interleukin-2 (rIL-2).

The magnetic bead:DR2:MBP84-102 complexes were incubated with donor cells for 20 minutes on ice in RPMI 1640 supplemented with 10% fetal bovine serum, 2 µM L-glutamine, and 10 µg/ml phytohemaglutinin. Beads with cells attached were separated magnetically, washed four times with the incubation medium and then maintained in incubation medium supplemented with 20 U/ml rIl-2.

After seven days, the isolated T cells were challenged with MBP84-102 and autologous APCs. In triplicate culture $10^3$ T cells were cultured with $5 \times 10^5$ freshly irradiated autologous APCs (peripheral blood lymphocytes) in the presence of increasing concentrations of MBP84-102. During the final 8 hours of a 72 hour incubation at 37° C., 1 µCi of [$^3$H]-thymidine was added and the degree of proliferation was measured by incorporated radioactivity. The T cell proliferation rate showed a dose dependent response to MBP84-102 and autologous APCs indicating the presence of T cells specific to MBP84-102 (FIG. 1).

The precursor cell frequency in a normal individual is approximately one in a million. The magnitude of response following an initial stimulation/antigen-specific proliferation assay is too great to be accounted for by differential proliferation of the DR2 specific T cells without actual isolation and enrichment of the population for those cells.

EXAMPLE 2

Antigen Specificity of the Isolated T Cells

T cells presumably specific to MBP(84-102) were isolated as described in Example 1. The isolated T cells were cultured in triplicate with $5 \times 10^5$ freshly irradiated autologous APC cells in the presence of 0, 5, 10, and 20 µg/ml of either 6×His-MBP(83-102)YH$^{83}$ peptide, MBP(84-102) or with irrelevant peptide MBP(124-143). The degree of T cell proliferation was measured by [$^3$H]-thymidine incorporation.

Figure 2:
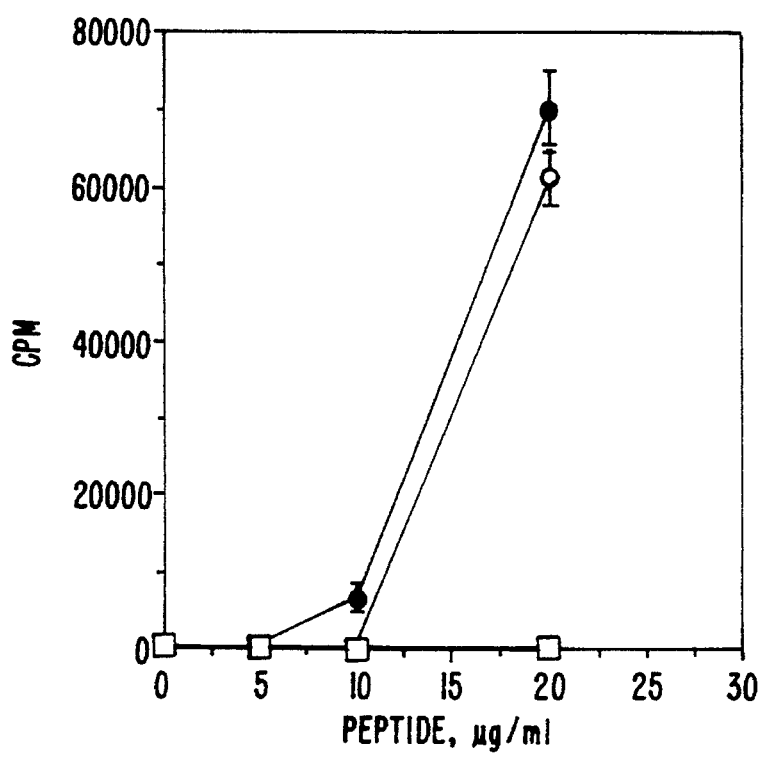
FIG. 2 shows the proliferative response of T cells to MBP(84-102) peptides (○), [6×His-MBP(83-102)Y$^{83}$]peptides (●), and irrelevant MBP(124-143) peptides (□).

FIG. 2 shows the antigen specificity of the isolated T cells. The cells proliferated in the presence of peptides containing the epitope MBP(84-102), yet failed to proliferate in the presence of another epitope MBP(124-143) from the same myelin basic protein under identical conditions. Thus, the claimed method isolated MBP(84-102) specific T cells.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of detecting the presence of antigen presenting cells bearing a pre-selected MHC:antigen complex in a biological sample suspected of comprising said antigen presenting cells, said method comprising the steps of:

(a) providing T cells specific for the MHC:antigen complex;

(b) contacting said biological sample with the T cells; and (c) detecting changes in the proliferation rate of said T cells (d) relating the changes in proliferation rate of said to T cells to the presence in said biological sample of antigen presenting cells bearing the pre-selected MHC:antigen complex.

2. The method of claim 1 wherein said T cells are specific for a single MHC:peptide complex.

3. The method of claim 1 wherein said T cells are human T cells.

4. The method of claim 1 wherein said detecting comprises the steps of:
   (a) contacting said T cells with a labeled metabolic substrate; and
   (b) measuring the rate of uptake of said metabolic substrate by the T cells.

5. The method of claim 1, wherein said T cells specific for the MHC:antigen complex are isolated by a method comprising the steps of:
   (a) providing an isolated MHC:peptide complex wherein said complex is bound to a solid support;
   (b) contacting the complex with a biological source containing T cells to form an MHC:peptide:T cell complex;
   (c) removing the MHC:peptide:T cell complex from the biological source; and
   (d) separating T cells from the MHC:peptide:T cell complex.

6. The method of claim 1, wherein said antigen presenting cells are associated with an autoimmune disease.

7. The method of claim 6, wherein said autoimmune disease is multiple sclerosis.

* * * * *